United States Patent [19]

Andriska et al.

[11] 4,046,773
[45] Sept. 6, 1977

[54] CARBAMOYL-IMIDAZOLE DERIVATIVE HAVING PESTICIDAL ACTIVITY

[75] Inventors: Viktor Andriska; Katalin Görög née Privitzer; Györgyi Bruckner; Zsuzsanna Nemessányi née Székely; Miklós Havasi, all of Budapest; Bela Ráskay, Veszprem; Erzsébet Grega née Tóth, Miskolc; Teréz Szigeti née Haranghy, Miskolc; Jozsef Dudás, Miskolc; Gyula Szilágyi, Miskolc; Sandor Marosvölgyi, Miskolc; Pál Gribovszky, Miskolc; Zoltán Pintér, Miskolc; Győző Bors, Miskolc, all of Hungary

[73] Assignees: Nehezvegyipari Kutato Intezet, Veszprem; Eszakmagyarorszagi Vegyimuvek, Sjobabony, both of Hungary

[21] Appl. No.: 370,620

[22] Filed: June 18, 1973

[51] Int. Cl.$^2$ .................................... C07D 233/66
[52] U.S. Cl. .................... 548/339; 424/273 R; 548/341; 548/333
[58] Field of Search ........................... 260/309, 309.2

[56] References Cited

U.S. PATENT DOCUMENTS

| 3,491,098 | 1/1970 | Archer | 260/268 |
| 3,821,393 | 6/1974 | Janiak et al. | 424/273 |
| 3,868,458 | 2/1975 | Baker et al. | 424/273 |

FOREIGN PATENT DOCUMENTS

| T5998 | 4/1973 | Hungary | 260/309 |
| 5,998 | 7/1971 | Hungary | 260/309 |
| 1,151,424 | 5/1969 | United Kingdom | 260/309.2 |

OTHER PUBLICATIONS

Zalikin, et al., C. A. 75:87741n (1971).
Staab, et al., C. A. 57:4649–4650 (1962).

*Primary Examiner* — Cecilia M. S. Jaisle
*Attorney, Agent, or Firm* — Young & Thompson

[57] ABSTRACT

New substituted carbamoylimidazole derivatives of the general formula (I)

$$\begin{array}{c} N \longrightarrow C-R_2 \\ \parallel \quad \quad \parallel \\ R_1-C \quad \quad C-R_3 \\ \diagdown N \diagup \\ | \\ C=O \\ | \\ NH \\ | \\ R_4 \end{array} \quad (I)$$

have been prepared by reacting the appropriate substituted imidazole derivatives of the general formula (II)

$$\begin{array}{c} N \longrightarrow C-R_2 \\ \parallel \quad \quad \parallel \\ R_1-C \quad \quad C-R_3 \\ \diagdown N \diagup \\ H \end{array} \quad (II)$$

with isocyanate compounds of the general formula (III)

$$R_4-N=C=O \quad (III).$$

The new compounds of the general formula (I) are potent herbicides and fungicides.

In the above formulae
$R_1$ stands for hydrogen atom or methyl group,
$R_2$ and $R_3$ each may represent a hydrogen atom or a nitro group, or $R_2$ and $R_3$ may form together a —CH=CH—CH=CH— group, which forms a six-membered ring together with the adjacent carbon atoms of the imidazole ring, and
$R_4$ stands for a cyclohexyl, phenyl, chlorophenyl or dichlorophenyl group.

3 Claims, No Drawings

CARBAMOYL-IMIDAZOLE DERIVATIVE HAVING PESTICIDAL ACTIVITY

This invention relates to novel carbamoyl-imidazole derivatives possessing pesticidal activities.

The new compounds according to the invention correspond to the general formula (I)

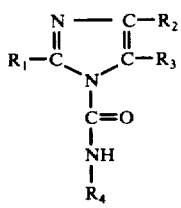

(wherein
  $R_1$ stands for hydrogen atom or methyl group,
  $R_2$ and $R_3$ each may represent a hydrogen atom or a nitro group, or $R_2$ and $R_3$ may form together a —CH=CH—CH=CH— group, which together with the adjacent carbon atoms of the imidazole ring forms a six-membered ring, and
  $R_4$ stands for a cyclohexyl, phenyl, chlorophenyl or dichlorophenyl group.)

The pesticides containing the compounds of the general formula (I) as active agents can be used for combatting weeds and fungi proliferating among the field crops.

As it is known, some imidazole derivatives possess fungicidal activities (Wellmann, McCallon: Contr. Boyce Thompson Inst. 1946, 14 151). 2-Heptadecyl-2-imidazoline acetate, sold under the trade name CLYODIN is used e.g. in the United States against apple phusycladium. The activity of unsubstituted imidazole has also been tested, this compound, however, proved to be inactive. According to the biological tests the efficiency of the substituted imidazole derivatives depends on the number of carbon atoms contained in the side chain, and the most advantageous derivatives have a side chain of 13 to 17 carbon atoms.

Another imidazole derivative of fungicidal activity, 2-(2-furyl)-benzimidazole, was prepared and sold by Bayer A.G.

Besides these fungicides, imidazole derivatives of herbicidal activities have also been prepared. Such compounds are e.g. the 2-trifluoromethyl-benzimidazole and its derivatives which can be used for combatting annual dicotyledons proliferating among the cereals.

Dutch Patent Specifications Nos. 64 07401 and 65 10168 describe substituted imidazole derivatives of herbicidal activities, wherein alkyl, aryl, nitrile, cyano or halogen substituents are attached to the carbon atoms of the five-membered imidazole ring.

Hungarian Patent Specification No. 158 002 describes the preparation of nitro-substituted imidazole carbamates, wherein the carbamate group is attached in position 2 in the imidazole ring.

These various imidazole compounds, however, couldnot come into general use either as herbicides or as fungicides. This can mainly attributed to the fact that according to the investigations of Van der Kerk et al. only a limited number of the various 2-alkyl-2-imidazoline acetates possess potent fungicidal activities. Namely, these authors have stated that fungicidal activity could only be detected at compounds containing a $C_{13-15}$ alkyl side chain.

The herbicidal activities of various alkyl-aryl-urea derivatives were recognized even before the detection of the imidazole herbicides. Their most commonly used representatives, i.e. the N-substituted phenyl-N-alkoxy-N-alkyl-urea compounds (see e.g. German Patent Specifications Nos. 1,076,117 and 1,028,986, as well as U.S. Pat. No. 2,960,534) show, however, no selectivity in biological sense. Using these compounds a selective control of weeds can only be attained when accurately predetermined doses are employed, and when no toxic amounts of the active agents can reach the roots of the cultivated plants shown in greater depths.

Now we have found, unexpectedly, that the novel substituted carbamoyl-imidazole derivatives of the general formula (I) — wherein $R_1$, $R_2$, $R_3$ and $R_4$ each have the same meanings as defined above — possess excellent fungicidal and herbicidal activities together with a high degree of selectivity. These compounds, when admixed with the soil, are absorbed by the roots of the weeds and exert efficient herbicidal activities prior to their emergency, and maintain their effectiveness during the whole growth season of the cultivated plants. The new compounds proved to be equally effective against both dicotyledons and monocotyledons, while they show no phytotoxic effects with respect to the cultivated plants.

Among the weeds which can effectively be controlled using the new herbicides the following are to be mentioned:

a. monocotyledons, such as foxtail (*Echinochloa crusgalli*), greengrass (*Setaria viridis*), (*Setaria glauea*), meadow foxtail (*Alopecurua pratensis*), meadow-gras (*Poa pratensis*), and b. dicotyledons, such as amaranth (*Amaranthus retroflexus*), white pigweed (*Chenopodium album*), morning glory (*Polygonum convulus*) and heckle-mustard (*Raphanus raphanistrum*).

The herbicidal or fungicidal compositions may contain the compounds of the general formula (I) as such or together with the usual carriers, diluents, emulsifying agents, lubricants, wetting agents etc., and can be formulated into powder sprays, emulgeable concentrates, etc. These compositions contain at least one compound of the general formula (I) as active agent in an amount of 0.5 to 90% by weight. The herbicidal or fungicidal compositions are prepared according to methods well known in the art.

According to our observations a dose of 4 to 6 kg./ha. of a powder spray containing a compound of the general formula (I) in an amount of 50% by weight can be used satisfactorily for combatting both dicotyledons and monocotyledons.

A selective herbicidal activity was determined for the compounds of the general formula (I) with respect to corn (Zea mays), sunflower (*Helianthus annuus*), potato (*Solanum tuberosum*), sorghum (Sorghum) and jungle rice (*Panicum*). No phytotoxic effects could be observed when these plants were treated with the active agents in doses of as high as 10 kg./ha.

We have observed further that some substituted carbamoyl-imidazole derivatives of the general formula (I) possess excellent fungicidal activities too. In biological tests using Altenaria tenusis as test organism these new substituted carbamoyl imidazoles showed significantly better results than N-(trichloromethyl-thio)-phthalimide, a known fungicide sold under the trade name CAP-FALTAN.

The toxicities of the new compounds having the general formula (I) with respect to humans and warm-blooded animals are negligible. The acute oral $LD_{50}$ values of the new compounds were around 3500 to 3800 mg./kg. measured on rats.

The new substituted carbamoyl-imidazole derivatives of the general formula (I) can easily be prepared by reacting a substituted imidazole compound of the general formula (II)

$$R_1-C\underset{\underset{H}{\overset{|}{N}}}{\overset{N \underline{\qquad} C-R_2}{\underset{C-R_3}{\|}}}$$ (II)

with an isocyanate of the general formula (III)

$$R_4-N=C=O$$ (III).

The reaction can be carried out in water or in polar organic solvents, as well as in an aqueous-organic emulsion. The reaction proceeds even at room temperature, and in some instances it is slightly exothermic. In order to ensure a complete reaction elevated temperatures can also be used, the reaction temperature, however, may not exceed the boiling point of the solvent used. The starting compounds of the general formulas (II) and (III) can be used in equimolar amounts, or one of them can be added in a slight excess of about 5 to 10%.

In the majority of the cases the reaction takes place spontaneously, in some instances, however, it is preferable to add a catalyst to the mixture. As catalyst, e.g. tertiary amines, such as triethylamine can be used.

The above reaction provides the appropriate substituted carbamoyl-imidazoles with yields of about 70 to 95%. The purity grade of the thus-obtained products meets the requirements of agricultural use, accordingly they can be converted into pesticidal formulations without any purification step.

The invention is elucidated in detail by the aid of the following non-limiting examples.

EXAMPLE 1

1-Phenylcarbamoyl-2-methyl-imidazole

A solution of 11.9 g. (0.1 mol.) of phenylisocyanate in 120 ml. of toluene is added to the stirred solution of 8.61 g. (0.105 mol.) of 2-methyl-imidazole in 60 ml. of water under cooling at a temperature of 10 to 12° C. The reaction mixture is stirred at room temperature for one hour, thereafter the separated product is filtered off, washed an dried. 14.0 g. (69.6%) of 1-phenylcarbamoyl-2-methyl-imidazole are obtained; m.p.: 205°–207° C.

Analysis: Calculated: N = 20.88%. Found: N = 20.1%.

EXAMPLE 2

1-Phenylcarbamoyl-2-methyl-5-nitroimidazole

A solution of 11.9 g. (0.1 mol.) of phenylisocyanate in 75 ml. of toluene is added dropwise to the stirred suspension of 15.2 g. (0.12 mol.) of 2-methyl-5-nitroimidazole in 60 ml. of water at 10° to 12° C. When the addition is complete, the mixture is stirred for further 4 hours. The separated product is filtered off, washed and dried. 20.4 g. (82.9%) of 1-phenylcarbamoyl-2-methyl-5-nitroimidazole are obtained; m.p.: 218°–220° C.

Analysis: Calculated: N = 22,76%. Found: N = 20.0%.

EXAMPLE 3

1-(4-Chlorophenyl(-carbamoyl-2-methylimidazole

A solution of 15.3 g. (0.1 mol.) of 4-chlorophenyl-isocyanate in 120 ml. of toluene is added dropwise to the stirred solution of 8.61 g. (0.105 mol.) of 2-methyl-imidazole in 60 ml. of water at 10° to 12° C, under cooling. The reaction mixture is stirred at room temperature for one hour. The separated product is filtered off, washed with water and dried. 17.4 g. (74%) of 1-(4-chlorophenyl)-carbamoyl-2-methylimidazole are obtained; m.p.: 138°–140° C.

Analysis: Calculated: Cl = 15.05%; N = 17.83%. Found: Cl = 15.08%; N = 17.5%.

EXAMPLE 4

1-(4-Chlorophenyl)-carbamoyl-2-methyl-5-nitroimidazole

A solution of 15.3 g. (0.1 mol.) of 4-chlorophenyl-isocyanate in 75 ml. of toluene is added dropwise to the stirred suspension of 15.2 g. (0.12 mol.) of 2-methyl-5-nitroimidazole in 60 ml. of water at 10° to 12° C, under cooling. When the addition is complete, the mixture is stirred for further 4 hours. Thereafter the separated product is filtered off, washed and dried. 25.15 g. (89.7%) of crystalline 1-(4-chlorophenyl)-carbamoyl-2-methyl-5-nitroimidazole are obtained; m.p.: above 240° C.

Analysis: Calculated: N = 19.96%; Cl = 12.64%. Found: N = 20.07%; Cl = 12.07%.

EXAMPLE 5

1-(3,4-Dichlorophenyl)-carbamoyl-2-methylimidazole

A solution of 8.61 g. (0.105 mol.) of 2-methylimidazole in 60 ml. of water is added dropwise to the stirred solution of 18.8 g. (0.1 mol.) of 3,4-dichlorophenyl-isocyanate in 120 ml. of toluene at 10° to 12° C under cooling. The reaction mixture is stirred at room temperature for one hour. The separated product is filtered off, washed and dried. 22.0 g. (81.5%) of 1-(3,4-dichlorophenyl)-carbamoyl-2-methylimidazole are obtained; m.p.: 140° C.

Analysis: Calculated: N = 15.56%; Cl = 26.25%. Found: N = 15.09%; Cl = 26.5%.

EXAMPLE 6

1-(3,4-dichlorophenyl)-carbamoyl-2-methyl-5-nitroimidazole

A solution of 18.8 g. (0.1 mol.) of 3,4-dichlorophenyl-isocyanate in 75 ml. of toluene is added dropwise to the stirred suspension of 15.2 g. (0.12 mol.) of 2-methyl-5-nitroimidazole in 60 ml. of water. When the addition is complete the reaction mixture is stirred at room temperature for further 4 hours. The separated product is filtered off, washed and dried. 27.8 g. (88.5%) of 1-(3,4-dichlorophenyl)-carbamoyl-2-methyl-5-nitroimidazole are obtained; m.p.: above 204° C.

Analysis: Calculated: N = 17.78%; Cl = 22.51%. Found: N = 17.99%; Cl = 19.90%.

EXAMPLE 7

1-(4-chlorophenyl)-carbamoyl-benzimidazole 15.3 g. (0.1 mol.) of 4-chlorophenyl-isocyanate and 0.5 g. of triethylamine are added at room temperature to the stirred suspension of 12.4 g. (0.105 mol.) of benzimidazole in 200 ml. of toluene. The reaction mixture is boiled with stirring for one hour, thereafter it is cooled, the separated product is filtered off, washed and dried. 25.3 g. (93.1%) of 1-(4-chlorophenyl)-carbamoyl-benzimidazole are obtained. The white, crystalline product melts at 175° C.

Analysis: Calculated: Cl = 13.04%. Found: Cl = 12.33%.

EXAMPLE 8

1-(3,4-dichlorophenyl)-carbamoyl-benzimidazole 18.8 g. (0.1 mol.) of 3,4-dichlorophenyl-isocyanate and 0.5 g. of triethylamine are added at room temperature to the stirred suspension of 12.4 g. (0.105 mol.) of benzimidazole in 200 ml. of toluene. The reaction mixture is boiled for 30 minutes with stirring, thereafter it is allowed to cool. The separated product is filtered off, washed and dried. 28.4 g. (92.8%) of 1-(3,4-dichlorophenyl)-carbamoyl-benzimidazole are obtained. The white, crystalline product melts at 182° C.

Analysis: Calculated: Cl = 23.16%. Found: Cl = 22.65%.

EXAMPLE 9

1-Cyclohexylcarbamoyl-2-methylimidazole

To a 8 to 12° C solution of 9.8 g. (0.12 mol.) of 2-methylimidazole in 100 ml. of water there are added 12.5 g. (0.1 mol.) of cyclohexylisocyanate, followed by 0.5 g. of triethylamine. Upon the addition of the triethylamine catalyst the reaction immediately sets in, and a precipitate start to separate. The reaction mixture is stirred at room temperature for 3 hours. Thereafter the separated product is filtered off, washed and dried. 16.4 g. (80.0%) of 1-cyclohexylcarbamoyl-2-methylimidazole are obtained; m.p.: 100°–102° C.

Analysis: Calculated: N = 20.27%. Found: N = 20.0%.

EXAMPLE 10

1-(4-Chlorophenyl)-carbamoyl-2-methyl-5-nitroimidazole

A solution of 17.0 g. (0.11 mol.) of 4-chlorophenyl-isocyanate in 71 ml. of tetrahydrofuran is added at room temperature to the stirred suspension of 12.7 g. (0.1 mol.) of 2-methyl-5-nitroimidazole and 0.5 g. of triethylamine in 70 ml. of tetrahydrofuran. A slightly exothermic reaction sets in, which terminates after 4 hours of stirring. The separated product is filtered off, washed with toluene and dried. 25 g. (89.5%) of 1-(4-chlorophenyl)-carbamoyl-2-methyl-5-nitroimidazole are obtained. The white, crystalline substance melts above 240° C.

Analysis: Calculated: N = 19.96%; Cl = 12.23%. Found: N = 20.78%; Cl = 12.64%.

EXAMPLE 11

Powder spray 100 g. of 1-(4-chlorophenyl)-carbamoyl-2-methylimidazole (prepared as described in Example 3) are admixed with 5 g. of sodium oleyl-methyl-tauride and 95 g. of active silica gel to give a powder spray.

EXAMPLE 12

Powder spray 100 g. of 1-(3,4-dichlorophenyl)-carbamoyl-2-methylimidazole (prepared as described in Example 5) are admixed with 10 g. of Arkopon T, fatty alcohol sulfate, 10 g. of powdery sulfite waste liquor and 80 g. of powdery chalk to give a powder spray.

EXAMPLE 13

Powder Spray

A mixture of 100 g. of 1-(3,4-dichlorophenyl)-carbamoyl-2-methyl-5-nitroimidazole (prepared as described in Example 6), 5 g. of sodium oleyl-methyl-tauride and 95 g. of active silica gel is finely ground and homogenized. A powder spray containing 50% of the active agent is obtained.

EXAMPLE 14

Powder spray

A mixture of 100 g. of 1-(3,4-dichlorophenyl)-carbamoyl-benzimidazole, 80 g. of kaoline, 10 g. of powdery sulfite waste liquor and 10 g. of powdery fatty alcohol sulfate is finely ground and homogenized to give a powder spray.

EXAMPLE 15

Powder spray

A mixture of 100 g. of 1-(4-chlorophenyl)-carbamoyl-benzimidazole, 40 g. of attapulgite, 40 g. of kaoline, 10 g. of powdery sulfite waste liquor and 10 g. of sodium oleyl-methyl-tauride is finely ground and homogenized to give a powder spray.

EXAMPLE 16

Powder spray 50 g. of 1-(3,4-dichlorophenyl)-carbamoyl-2-methyl-5-nitroimidazole and 50 g. of 1-(4-chlorophenyl)-carbamoyl-benzimidazole are mixed with 95 g. of Ultrasil (active silica gel) and 5 g. of sodium oleyl-methyl-tauride, and the mixture is micronized. A powder spray of 50% active agent content is obtained.

EXAMPLE 17

Powder spray 50 g. of 1-(4-chlorophenyl)-carbamoyl-benzimidazole and 50 g. of N-isopropyl-chloroacetanilide are mixed with 80 g. of Ultrasil (active silca gel), 10 g. of Totanin B (powdery sulfite waste liquor) and 10 g. of sodium oleyl-methyl-tauride, and the mixture is ground in a ball mill. A powder spray of 50% active agent content is obtained.

EXAMPLE 18

Examination of Phytotoxicity on Corn

The respective compounds of the general formula (I) were treated as described in Examples 11 to 15 to give powder sprays of 50% active agent content. These formulations were sprayed onto corn in amounts of 10 kg./ha. No depressive activity was observed.

| Formulation | Length of corn stem % | Length of corn root % |
| --- | --- | --- |
| Example 11 | 106.8 | 116.8 |
| Example 12 | 117.3 | 112.7 |
| Example 15 | 125.9 | 146.8 |
| Untreated control | 100 | 100 |

EXAMPLE 19

Weed Control Experiments in Potato

The herbicidal activities of the formulations according to the invention were tested in potato. As reference substances two compounds having been already introduced into the large-scale cultivation, namely Afalon (N-/4-chlorophenyl/-N-methoxy-N-methylurea) and Aresin (N-/3,4-dichlorophenyl/-N-methoxy-N-methylurea) were used. In the open-air experiments parcels of 5×5 m. were treated. Potato was planted in row spaces of 70×50 cm. in the parcels. The parcels were randomized and treated prior to emergence with a powder spray containing 50% of the respective active agent. 4 kg./ha. of doses were used, and the treatment was repeated four times.

The results are summarized in the following Table.

| Herbicide | Amount of weeds, % |
| --- | --- |
| Afalon | 12 |
| Aresin | 15 |
| Example 11 | 10 |
| Example 12 | 7 |
| Example 13 | 8 |
| Untreated control | 100 |

EXAMPLE 20

Weed Control Experiments in Corn

The open-air experiments were carried out on small parcels as described in Example 19. The parcels were treated with 5 kg./ha. of the respective herbicides containing 50% of active agent. The treatment was repeated five times. The weeds controlled in this experiment were identical to those listed on page 4 of the specification.

The results are summarized in the following Table.

| Herbicide | Amount of weeds, % | |
| --- | --- | --- |
| | Monocotyledons | Dicotyledons |
| Example 11 | 28.4 | 5.6 |
| Example 12 | 16.8 | 3.4 |
| Example 15 | 11.1 | 3.4 |
| Untreated control | 100 | 100 |

EXAMPLE 21

Examination of Fungicidal Activity

The experiments were carried out according to the modified McCallon drop culture technique, using increasing amounts of the active agents. As poisoning method, the so-called "dried spray technique" were used. The fungicidal activity was characterized by the inhibition of germination and the retardation of germ cyst growth. A suspension containing 70 to 80 conidia pro field of vision was mounted onto a microscopic slide. The slide was placed into a Petri-dish, and thermostated at 23 to 25° C for 24 hours. Thereafter the inhibition of germination and the germ cyst growth were examined microscopically, using a 150 fold magnification.

As test organism, Alternaria tenius NEES was used. In the experiments the compounds prepared as described in Examples Nos. 2, 6 and 10, respectively, were tested. As reference substances, Zineb and Ortocid were used.

The results of these experiments show that the compounds according to the invention possess significantly better germination-inhibiting and growth-inhibiting activities than the reference substances.

What we claim is:

1. 1-Phenylcarbamoyl-2-methyl-5-nitroimidazole.
2. 1-(4-chlorophenyl)-carbamoyl-2-methyl-5-nitroimidazole.
3. 1-(3,4-dichlorophenyl)-carbamoyl-2-methyl-5-nitroimidazole.

* * * * *